(12) United States Patent
Yakushiji et al.

(10) Patent No.: US 11,219,714 B2
(45) Date of Patent: Jan. 11, 2022

(54) LIQUID MEDICINE ADMINISTRATION DEVICE AND OPERATION METHOD THEREOF

(71) Applicant: TERUMO KABUSHIKI KAISHA, Tokyo (JP)

(72) Inventors: Yusuke Yakushiji, Kanagawa (JP); Junichi Ogawa, Yamanashi (JP)

(73) Assignee: TERUMO KABUSHIKI KAISHA, Tokyo (JP)

( * ) Notice: Subject to any disclaimer, the term of this patent is extended or adjusted under 35 U.S.C. 154(b) by 305 days.

(21) Appl. No.: 16/586,351

(22) Filed: Sep. 27, 2019

(65) Prior Publication Data

US 2020/0023118 A1 Jan. 23, 2020

Related U.S. Application Data

(63) Continuation of application No. PCT/JP2018/013558, filed on Mar. 30, 2018.

(30) Foreign Application Priority Data

Mar. 30, 2017 (JP) .............................. JP2017-066816

(51) Int. Cl.
*A61M 5/145* (2006.01)
*A61M 5/168* (2006.01)
(Continued)

(52) U.S. Cl.
CPC ........ *A61M 5/145* (2013.01); *A61M 5/16831* (2013.01); *A61M 5/31513* (2013.01);
(Continued)

(58) Field of Classification Search
CPC .................. A61M 5/142; A61M 5/145; A61M 2005/14208; A61M 2005/31588
See application file for complete search history.

(56) References Cited

U.S. PATENT DOCUMENTS

| 5,482,438 | A | 1/1996 | Anderson et al. |
| 7,959,609 | B2 * | 6/2011 | Gaydos .................. A61M 11/00 604/155 |

(Continued)

FOREIGN PATENT DOCUMENTS

| CN | 104640585 A | 5/2015 |
| EP | 3132820 A1 | 2/2017 |

(Continued)

OTHER PUBLICATIONS

International Searching Authority, Written Opinion issued in connection with PCT Application No. PCT/JP2018/013558, dated Jun. 19, 2018.

(Continued)

*Primary Examiner* — Laura A Bouchelle
(74) *Attorney, Agent, or Firm* — Foley & Lardner LLP

(57) ABSTRACT

A liquid medicine administration device includes: a cylinder filled with a liquid medicine, a gasket located inside the cylinder; an advancing mechanism configured to advance the gasket in a distal direction; a drive mechanism including a motor configured to drive the advancing mechanism; a battery configured to supply power to the motor; and a control unit configured to control a rotational speed of the motor. In a first movement period that is an initial sliding period included in an advancing movement of the gasket in the cylinder, a cycle including one continuous rotation and one continuous stoppage of the motor is repeated two or more times.

15 Claims, 12 Drawing Sheets

(51) Int. Cl.
*A61M 5/315* (2006.01)
*A61M 5/142* (2006.01)
(52) U.S. Cl.
CPC .............. *A61M 2005/14208* (2013.01); *A61M 2005/31588* (2013.01); *A61M 2205/33* (2013.01)

(56) References Cited

U.S. PATENT DOCUMENTS

| | | | |
|---|---|---|---|
| 8,523,803 B1 * | 9/2013 | Favreau ............ | A61M 5/14212 604/67 |
| 2015/0025499 A1 | 1/2015 | Trock et al. | |

FOREIGN PATENT DOCUMENTS

| | | | | |
|---|---|---|---|---|
| JP | 2004-516107 | A | 6/2004 | |
| JP | 2013-192850 | A | 9/2013 | |
| JP | 5777691 | B2 | 9/2015 | |
| JP | 2017-519532 | A | 7/2017 | |
| WO | WO-02/051471 | A1 | 7/2002 | |
| WO | WO-2014/045393 | A1 | 3/2014 | |
| WO | WO-2014045393 | A1 * | 3/2014 | ........ A61M 5/31511 |
| WO | WO-2015/102987 | A1 | 7/2015 | |

OTHER PUBLICATIONS

Extended European Search Report dated Sep. 21, 2020 in corresponding European Patent Application No. 18774993.2.
Office Action and Search Report in CN 201880020893.2, dated May 6, 2021 (17 pages).
International Searching Authority, "International Search Report," issued in connection with International Patent Application No. PCT/JP2018/013558, dated Jun. 19, 2018.
International Searching Authority, "Written Opinion," issued in connection with International Patent Application No. PCT/JP2018/013558, dated Jun. 19, 2018.

* cited by examiner

LIQUID MEDICINE ADMINISTRATION DEVICE AND OPERATION METHOD THEREOF

CROSS-REFERENCE TO RELATED APPLICATIONS

This is a bypass continuation of PCT Application No. PCT/JP2018/013558, filed on Mar. 30, 2018, which claims priority to Japanese Application No. 2017-066816, filed on Mar. 30, 2017. The contents of these applications are hereby incorporated by reference in their entireties.

BACKGROUND

The present disclosure relates to a liquid medicine administration device for expelling a liquid medicine from a cylinder and administering the liquid medicine to a living body, and an operation method thereof.

A syringe pump type liquid medicine administration device for expelling a liquid medicine filled in a cylinder with a plunger and administering the liquid medicine into a living body has been conventionally known. This type of liquid medicine administration device includes a barrel-type cylinder, a gasket placed in the cylinder in a slidable manner, a plunger for advancing the gasket, and a motor serving as a drive source for advancing the plunger (see, for example, Japanese Patent No. 5777691). It is known that, when the liquid medicine administration device is stored for several months with the gasket being placed inside the cylinder in a state in which a liquid lubricant is applied to the inner peripheral surface of the cylinder or the outer peripheral surface of the gasket in order to allow the gasket to slide inside the cylinder, the sliding resistance of the gasket inside the cylinder is greater in a period (initial sliding period) from when the gasket starts advancing in the cylinder until the gasket advances a predetermined distance, while the sliding resistance is smaller in a period (normal sliding period) following the initial sliding period.

SUMMARY

Heretofore, a driving force (thrust) required to advance the plunger by driving of the motor has been very high in the initial sliding period. In order to reliably obtain such high driving force, it is necessary to increase a size of the motor and the battery, which may lead to an increase in the size of the entire liquid medicine administration device.

Certain embodiments of the present invention have been developed in consideration of such problems, and an object of certain embodiments is to provide a liquid medicine administration device that supresses an increase in driving force in an initial sliding period and is smaller in size than the conventional device, and an operation method thereof.

In one aspect of the present invention, a liquid medicine administration device for administering a liquid medicine into a living body includes: a cylinder filled with the liquid medicine; a gasket placed inside the cylinder in a slidable manner; a liquid lubricant applied to an inner peripheral surface of the cylinder or an outer peripheral surface of the gasket; an advancing mechanism for advancing the gasket in a distal direction; a drive mechanism including a motor that drives the advancing mechanism; a battery that supplies power to the motor; and a control unit that controls a rotational speed of the motor, wherein an advancing movement of the gasket within the cylinder includes a first movement period from when a part of the gasket starts moving until the gasket entirely starts moving, and a second movement period following the first movement period, and the control unit includes a program set such that one cycle including one continuous rotation and one continuous stoppage of the motor is repeated two or more times in the first movement period.

According to the liquid medicine administration device described above, the gasket is advanced at intervals in the first movement period that is the initial sliding period of the gasket, whereby, even if the sliding surface of the gasket adheres to the inner peripheral surface of the cylinder due to storage for long periods, the adhering portion is pulled off little by little. Thus, an excessive rise in sliding resistance in the initial sliding period can be suppressed. Accordingly, it is possible to provide a liquid medicine administration device that can suppress an increase in driving force in the initial sliding period and that is smaller in size than the conventional one.

The program may be set such that, in the one cycle, a stop time in which the motor is stopped is 1 to 55 times an operation time in which the motor is rotated.

According to this configuration, because the stop time of the motor in one cycle is appropriately long, the adhering portion of the gasket can be more reliably pulled off little by little, and an excessive rise in the sliding resistance in the initial sliding period can be further suppressed.

The program may be set such that the stop time of the motor in the one cycle is within a range of 0.25 to 17.68 seconds.

According to this configuration, because the stop time of the motor in one cycle is appropriately long, the adhering portion of the gasket can be more reliably pulled off little by little, and an excessive rise in the sliding resistance in the initial sliding period can be further suppressed.

The program may be set such that an advancing speed of the gasket according to calculation in the first movement period is within a range of 1 to 20 mm/min.

With this configuration, the driving force required to advance the gasket in the first movement period is sufficiently reduced.

The program may be set such that an estimated advancing distance of the gasket calculated based on a rotation amount of the motor in the one cycle is within a range of 0.01 to 0.1 mm.

With this configuration, the driving force required to advance the gasket in the first movement period is sufficiently reduced.

The control unit may include a rotation amount detection sensor that detects a rotation amount of the motor, and the program may be set such that, in the one cycle, the rotation of the motor is stopped for a predetermined time when a rotation amount of the motor detected by the rotation amount detection sensor after the motor starts rotating reaches a predetermined value corresponding to the estimated advancing distance of the gasket.

The control unit may control the operation of the motor such that an advancing speed of the gasket in the second movement period is faster than an advancing speed of the gasket in the first movement period.

The present inventor has found that the initial sliding resistance of the gasket in the cylinder differs depending on the moving speed of the gasket, and the initial sliding resistance tends to increase as the moving speed of the gasket is faster, while the sliding resistance afterward does not tend to depend on the moving speed of the gasket. In view of this, the gasket is moved slowly in the first movement period where the initial sliding resistance occurs, and the gasket is moved quickly in the following second movement period. Therefore, the driving force (thrust) required to advance the gasket in the first movement period is suppressed, whereby a desired administration rate is achieved without an increase in power consumption.

The motor may be a stepping motor, the control unit may control a frequency of a pulse transmitted to the motor, and the program may be set such that, in the one cycle, the rotation of the motor is stopped for a predetermined time when the number of pulses transmitted to the motor reaches a predetermined value corresponding to the estimated advancing distance of the gasket after the motor starts rotating.

Another aspect of the present invention provides an operation method of a liquid medicine administration device including: a cylinder that is filled with a liquid medicine and includes a liquid lubricant applied on an inner peripheral surface; a gasket placed inside the cylinder in a slidable manner; an advancing mechanism for advancing the gasket in a distal direction; a drive mechanism including a motor that drives the advancing mechanism; a battery that supplies power to the motor; and a control unit including a program that controls an operation of the motor, wherein an advancing movement of the gasket within the cylinder includes a first movement period from when a part of the gasket starts moving until the gasket entirely starts moving, and a second movement period following the first movement period, the method including repeating, two or more times, one cycle including one continuous rotation and one continuous stoppage of the motor in the first movement period.

In the one cycle, a stop time in which the motor is stopped may be 1 to 55 times an operation time in which the motor is rotated.

The stop time of the motor in the one cycle may be within a range of 0.25 to 17.68 seconds.

The control unit may include a rotation amount detection sensor that detects a rotation amount of the motor, and in the one cycle, the rotation of the motor may be stopped when an estimated advancing distance of the gasket calculated based on a rotation amount of the motor detected by the rotation amount detection sensor reaches a value within a range of 0.01 to 0.1 mm.

DETAILED DESCRIPTION

Preferred embodiments of a liquid medicine administration device and an operation method thereof according to the present invention will be described below with reference to the accompanying drawings.

Figure 1:
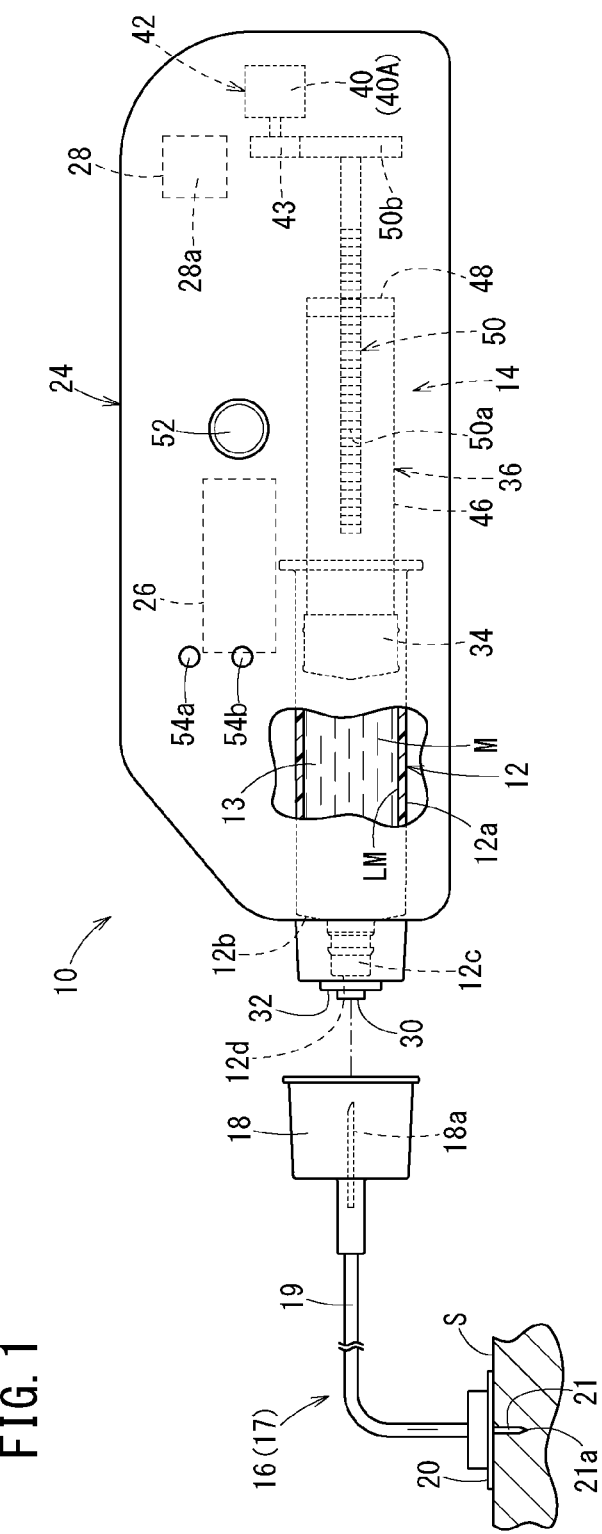
FIG. 1 is a schematic view of a liquid medicine administration device according to a first embodiment of the present invention.

A liquid medicine administration device 10 according to a first embodiment shown in FIG. 1 is used for injecting a liquid medicine M into a living body. The liquid medicine administration device 10 continuously administers the liquid medicine M filled in a cylinder 12 into a living body as a result of a pressing action on a plunger mechanism 14 over a relatively long time (for example, about several minutes to several hours). The liquid medicine administration device 10 may administer the liquid medicine M at intervals into a living body as well. Examples of the liquid medicine M include protein preparations, narcotic analgesics, and diuretics.

As shown in FIG. 1, when the liquid medicine administration device 10 is used, a patch-type needle-equipped tube 17, for example, is connected to the liquid medicine administration device 10 as an administration tool 16, and the liquid medicine M discharged from the cylinder 12 is injected into a body of a patient through the needle-equipped tube 17. The needle-equipped tube 17 includes a connector 18 connectable to a tip portion 12c of the cylinder 12, a flexible liquid delivery tube 19 having one end connected to the connector 18, a patch 20 connected to the other end of the liquid delivery tube 19 and attachable to a skin S, and a puncture needle 21 protruding from the patch 20. The puncture needle 21 substantially perpendicularly punctures the skin S. Note that the puncture needle 21 may obliquely puncture the skin S as well.

It is to be noted that the administration tool 16 to be connected to the liquid medicine administration device 10 is not limited to the patch-type needle-equipped tube 17 described above. For example, a puncture needle (such as a winged needle) may be connected to the tip of the liquid delivery tube 19. Alternatively, the administration tool 16 may be a bent needle connectable to the tip portion 12c of the cylinder 12 without passing through the liquid delivery tube 19. In this case, the bent needle is bent by, for example, approximately 90° downwards from the tip portion 12c of the cylinder 12 and perpendicularly punctures the skin S in conjunction with affixing (adhering) of the liquid medicine administration device 10 to the skin S. In addition, the tip portion 12c of the cylinder 12, the administration tool, and a part of the needle may be inside the cylinder 12, and the tip of the needle may protrude from the cylinder 12. In this case, the needle also perpendicularly punctures the skin S in conjunction with affixing (adhering) of the liquid medicine administration device 10 to the skin S.

The liquid medicine administration device 10 is provided with the cylinder 12 filled with the liquid medicine M, the plunger mechanism 14 for expelling the liquid medicine M from the cylinder 12, and a housing 24 that houses the cylinder 12 and the plunger mechanism. The housing 24 houses a battery 26 for supplying power necessary for operating the liquid medicine administration device 10, a control unit 28 (microcomputer) for performing various kinds of controls of the liquid medicine administration device 10, a speaker (not shown), and the like.

The cylinder 12 is formed into a hollow cylindrical shape and has a liquid medicine chamber 13 therein. The cylinder 12 has a body portion 12a having constant inner and outer diameters in the axial direction thereof and having a proximal end that is open, a shoulder portion 12b having inner and outer diameters reduced in a tapered shape from the tip of the body portion 12a in the distal direction, and the tip portion 12c protruding from the shoulder portion 12b in the distal direction. A liquid medicine discharge opening 12d communicating with the liquid medicine chamber 13 is formed in the tip portion 12c. A liquid lubricant LM (for example, silicone oil) is applied to the inner peripheral surface of the cylinder 12 (the inner peripheral surface of the body portion 12a).

The cylinder 12 is filled with the liquid medicine M in advance. The liquid medicine discharge opening 12d is sealed in a liquid-tight manner by a sealing member 30 made of an elastic resin material such as a rubber material or an elastomer material. The sealing member 30 is punctured by a needle 18a disposed in the connector 18 when the connector 18 shown in FIG. 1 is connected to the tip portion 12c. The sealing member 30 is fixed to the tip of the cylinder 12 by a cap 32 having an opening at the tip.

The plunger mechanism 14 includes a gasket 34 placed in the cylinder 12 in a slidable manner, an advancing mechanism 36 for advancing the gasket 34 in the distal direction, and a drive mechanism 42 having a motor 40 for driving the advancing mechanism 36.

Figure 2:
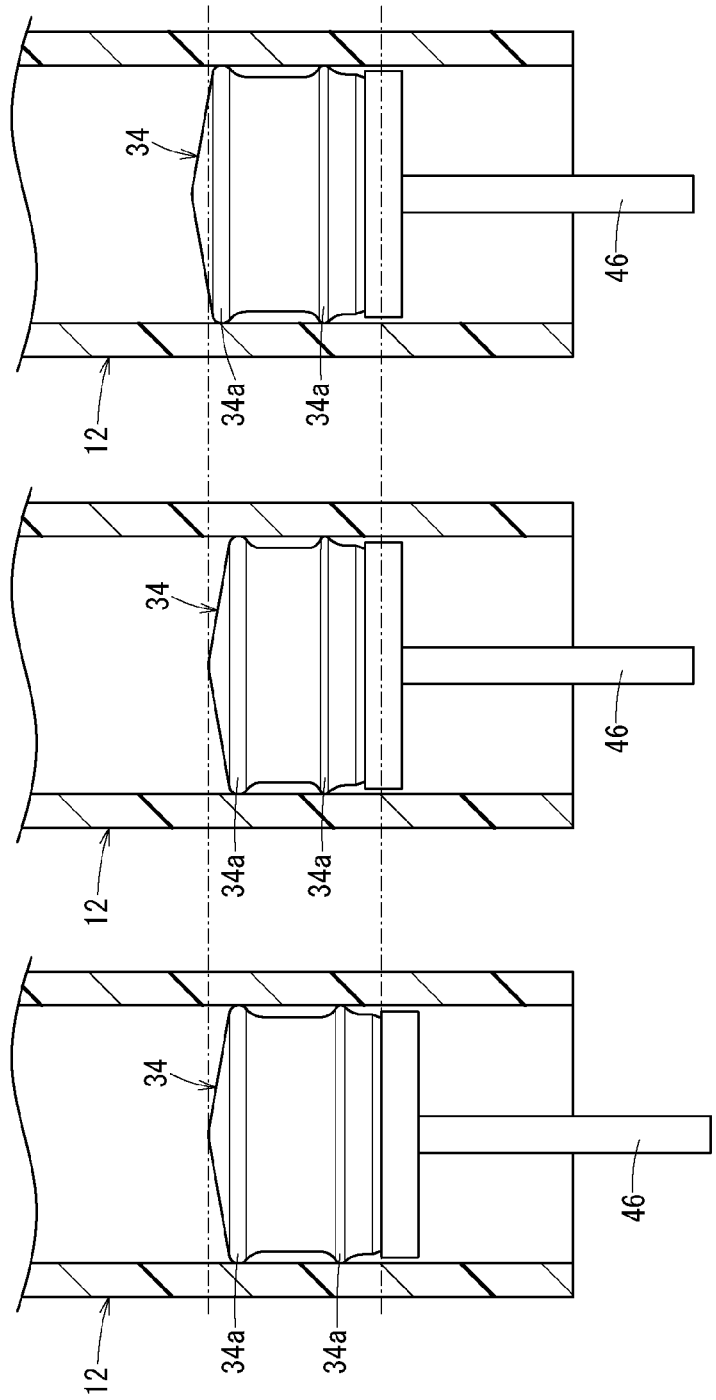
FIG. 2 is a schematic view for describing an initial sliding period of a gasket.

The gasket 34 is made of an elastic resin material such as a rubber material or an elastomer material, and the outer peripheral portion thereof is in close contact with the inner peripheral surface of the cylinder 12 (body portion 12a) in a liquid-tight manner. As a result, the proximal side of the liquid medicine chamber 13 is closed in a liquid-tight manner. As shown in FIG. 2, a plurality of (two in the illustrated example) annular protrusions 34a protruding outward in the radial direction is provided on the outer peripheral portion of the gasket 34 at intervals in the axial direction. The gasket 34 is placed in the cylinder 12 in a state where the annular protrusions 34a are elastically compressed and deformed by the inner peripheral surface of the cylinder 12. The liquid lubricant LM described above is applied over the entire circumference within at least a range in the axial direction in which the gasket 34 slides on the inner peripheral surface of the cylinder 12. The liquid lubricant LM may be applied only to an area around the gasket 34 at the initial position and the distal end side in the vicinity thereof. The liquid lubricant LM may be applied to the outer peripheral surface of the gasket 34.

In FIG. 1, the advancing mechanism 36 is axially movable with respect to the cylinder 12 and includes a plunger 46 for advancing the gasket 34 in the distal direction by pressing the gasket 34, a nut member 48 connected to the plunger 46 and formed with a female screw, and a feed screw 50 formed with a male screw 50a engaging with the female screw on the nut member 48. The plunger 46 is a member movable in the axial direction for expelling the liquid medicine M. The gasket 34 is connected to the tip of the plunger 46. As the plunger 46 advances, the gasket 34 is pressed by the plunger 46 in the distal direction, so that the gasket 34 advances.

The feed screw 50 is disposed along the axis of the cylinder 12. The feed screw 50 has a large gear 50b, which is a driven gear. The male screw 50a of the feed screw 50 is formed on the outer peripheral surface distal of the large gear 50b over a predetermined range in the axial direction. As the feed screw 50 rotates, the nut member 48 moves in the distal direction. At this time, the plunger 46 advances by being pushed in the distal direction by the nut member 48. Note that the female screw may be formed on the plunger 46 itself without providing the nut member 48.

The drive mechanism 42 has the motor 40, which is supplied with electric power from the battery 26 and driven and controlled under the control action of the control unit 28, and a pinion 43 fixed to an output shaft of the motor 40 and serving as a drive gear. The pinion 43 meshes with the large gear 50b of the feed screw 50.

The motor 40 is a rotational drive source that can be rotated faster with an increase in a control frequency and can be rotated slower with a decrease in the control frequency. In the present embodiment, the motor 40 is a stepping motor 40A that operates in synchronization with a pulse signal. The stepping motor 40A can control the rotational speed by changing the pulse frequency.

Note that, as the motor 40, another type of motor that can control rotational speed, such as an AC motor, a DC motor, or a brushless DC motor, may be used. The AC motor can change the rotational speed by changing an AC frequency. The DC motor can change the rotational speed by changing a motor voltage. The brushless DC motor can change the rotational speed by changing a pulse frequency.

The housing 24 is provided with a power button 52 for turning on or off a power source, and a plurality of light emitting units 54a and 54b.

The plurality of light emitting units 54a and 54b has a first light emitting unit 54a and a second light emitting unit 54b that emit different colors. The first light emitting unit 54a is a light emitting unit for indicating the operating state of the liquid medicine administration device 10, and can emit light of different colors. The second light emitting unit 54b is a light emitting unit that lights or flashes to indicate the occurrence of an error. The first light emitting unit 54a and the second light emitting unit 54b are composed of, for example, LEDs.

Next, the action of the liquid medicine administration device 10 configured as described above will be described.

When in use, the liquid medicine administration device 10 is taken out of a cold storage and left at normal temperature for a certain period of time (for example, 30 minutes) to be brought back to room temperature. Next, the surface (tip end surface) of the sealing member 30, which is a connection portion with the connector 18, is wiped off with alcohol cotton, for example, to disinfect the connection portion. Then, the administration tool 16 is connected to the liquid medicine administration device 10.

Next, the power button 52 is pressed. Then, the liquid medicine administration device 10 is mounted on the patient by attaching the device 10 to the skin S or clothes. Next, the puncture needle 21 punctures the skin S. Note that the liquid medicine administration device 10 may be attached to the patient before the puncture needle 21 punctures the skin S.

Next, delivery of liquid (administration of the liquid medicine M) is started. Specifically, the motor 40 is driven to transmit the rotational force from the pinion 43 to the feed screw 50 having the large gear 50b. As the feed screw 50 rotates, the nut member 48 engaged with the feed screw 50 advances, and the plunger 46 advances by being pushed by the nut member 48. Thus, the liquid medicine M in the cylinder 12 is expelled. The liquid medicine M expelled from the inside of the cylinder 12 is administered (injected) into the patient's body via the administration tool 16 puncturing the patient.

When the delivery of liquid is completed due to the plunger 46 advancing to a predetermined position, a sound indicating that the delivery of liquid is completed is output from a speaker built in the liquid medicine administration device 10, and the first light emitting unit 54a lights in a first color. When the delivery of liquid is completed, the puncture needle 21 is pulled out of the skin S (under the skin). Thereafter, the liquid medicine administration device 10 is thrown away.

Meanwhile, the advancing movement of the gasket 34 in the cylinder 12 has a first movement period (hereinafter referred to as an "initial sliding period") from when a part of the gasket 34 starts moving until the entire gasket 34 starts moving, a second movement period (hereinafter referred to as a "normal sliding period) following the first movement period.

The initial sliding period will be described with reference to FIG. 2 When the liquid medicine administration device 10 is stored for a long time, the sliding surface (two annular protrusions 34a in the illustrated example) of the gasket 34 adheres to the inner peripheral surface of the cylinder 12 as shown in FIG. 2 (on the left). As the plunger 46 advances, the gasket 34 starts to advance. Immediately after the gasket 34 starts to advance, only a part (the annular protrusion 34a on the proximal side) of the adhering portion is pulled off, whereby only a part of the gasket 34 advances, as shown in FIG. 2 (on the center). Then, when the entire adhering portion (the annular protrusions 34a on the distal side and the proximal side) is pulled off, the entire gasket 34 starts to advance (the gasket 34 transfer from the initial sliding period to the normal sliding period) as shown in FIG. 2 (on the right).

In the operation of the liquid medicine administration device 10 shown in FIG. 1, the rotational speed of the motor 40 is controlled by the control unit 28. Specifically, the control unit 28 has a program 28a set such that one cycle including one continuous rotation and one continuous stoppage of the motor 40 is repeated two or more times in the initial sliding period. The sliding resistance when the gasket 34 slides in the cylinder 12 is the highest in the initial sliding period.

The liquid medicine administration device 10 performs control to switch the rotational speed of the motor 40 (drive speed of the gasket 34). Hereinafter, the operation of the liquid medicine administration device 10 including such speed switching will be described in more detail.

Figure 3:
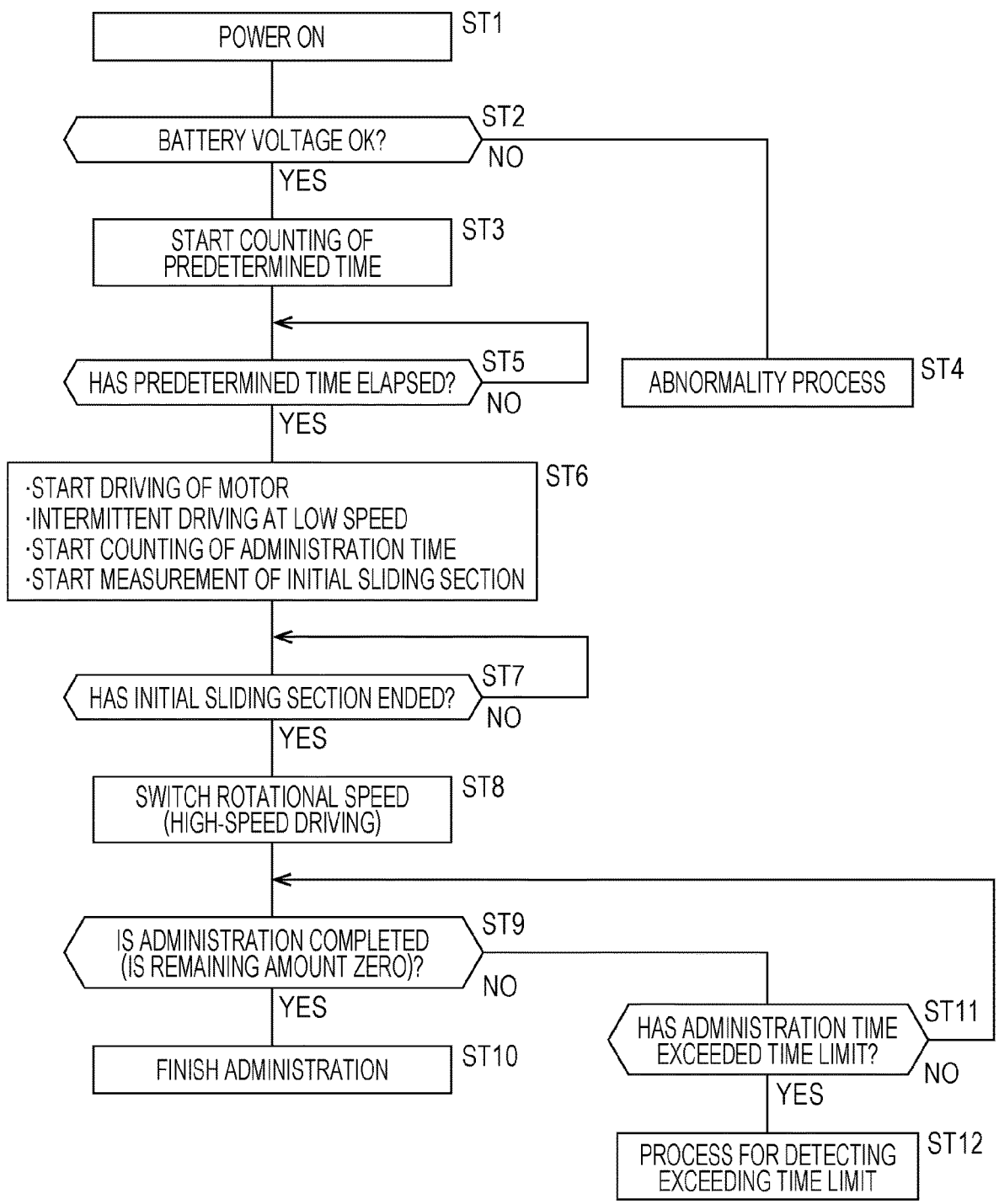
FIG. 3 is a flowchart for describing an operation of the liquid medicine administration device according to the first embodiment.

In FIG. 3, when the power button 52 (FIG. 1) of the liquid medicine administration device 10 is pressed and the power is turned on (step ST1), a process for checking a battery voltage is executed (step ST2). If it is determined that there is no abnormality in the battery voltage ("YES" in step ST2), a user is notified that there is no abnormality by lighting of the first light emitting unit 54a (or a buzzer sound output from the speaker), and counting of a predetermined time (for example, 5 minutes) is started (step ST3). Next, the liquid medicine administration device 10 is attached to the patient. When there is an abnormality in the battery voltage ("NO" in step ST2), an abnormality process is performed (step ST4). In the abnormality process, the second light emitting unit 54b lights or flashes to notify the user of an occurrence of abnormality. In the abnormality process, a buzzer sound may be output from the speaker.

When a predetermined time has elapsed after step ST3 ("YES" in step ST5), the control unit 28 of the liquid medicine administration device 10 drives the motor 40 to start administration at a first rotational speed S1 (initial sliding administration) (intermittent driving at low speed), starts counting of an administration time, and starts measurement of the initial sliding period (step ST6).

Next, the control unit 28 determines whether or not the initial sliding period has ended (whether the gasket 34 has moved a predetermined distance) (step ST7). In this case, the program 28a of the control unit 28 determines that the gasket 34 has passed the first movement period (determines that the initial sliding period has ended/the gasket 34 has moved a predetermined distance) based on, for example, the time in which the motor 40 operates at the first rotational speed S1. The stepping motor 40A used as the motor 40 rotates by a predetermined angle in one pulse, and a unit representing the number of pulses transmitted to the motor 40 in one second indicates a pulse frequency (pps). Therefore, the number of pulses transmitted to the stepping motor 40A is obtained by measuring the time in which the stepping motor 40A is operated at a predetermined pps, and the rotation amount can be determined by multiplying the number of pulses by a predetermined angle. When the stepping motor 40A is used as the motor 40, the distance the gasket 34 moves can be calculated by multiplying the rotation amount of the motor 40 by the distance the gasket 34 advances in one rotation of the motor 40. Therefore, whether or not the gasket 34 has moved a predetermined distance can be determined on the basis of the time during which the motor 40 operates at a predetermined speed (pps). When the stepping motor 40A is used as the motor 40, the program 28a of the control unit 28 may determine whether or not the gasket 34 has moved a predetermined distance on the basis of the rotation amount (the number of transmitted pulses) of the motor 40 operating at the first rotational speed S1.

When the initial sliding period has ended ("YES" in step ST7), the control unit 28 of the liquid medicine administration device 10 switches from low-speed driving to administration (high-speed driving) at a second rotational speed S2 (step ST8). When the administration at high-speed driving is performed, and the control unit 28 determines that the administration is completed (the remaining amount of the liquid medicine is zero) ("YES" in step ST9), the administration is finished (step ST10). In this case, the first light emitting unit 54a is turned off (or a buzzer sound is output from the speaker) to notify the user of the completion of administration. If it is not determined that the administration has been completed ("NO" in step ST9) and it is determined that the administration time exceeds a time limit ("YES" in step ST11), the control unit 28 performs a process for detecting exceeding time limit (step ST12). In the process for detecting exceeding time limit, the second light emitting unit 54b lights or flashes to notify the user of an occurrence of abnormality. In the process for detecting exceeding time limit, a buzzer sound may be output from the speaker.

The initial sliding period is considerably shorter than the normal sliding period, and the length thereof is within a range of, for example, 1.0 to 3.0 mm or 1.5 to 2.5 mm. The normal sliding period indicates a period in which the gasket 34 moves after the gasket 34 moves beyond the initial sliding period until the advancing movement of the plunger 46 is stopped with the completion of delivery of the liquid medicine M, and the length of the normal sliding period is within a range of, for example, 10 to 20 mm.

Figure 4:
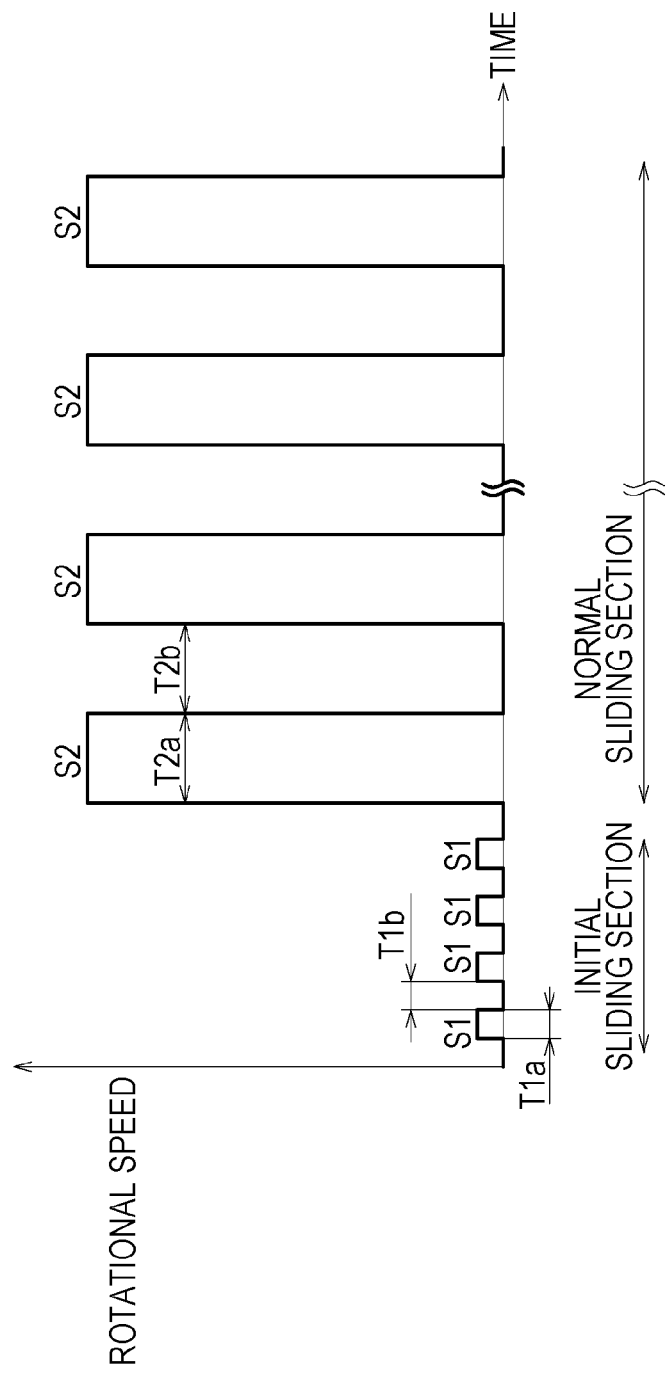
FIG. 4 is a first diagram for describing the action of the liquid medicine administration device according to the first embodiment.

FIG. 4 is a conceptual diagram (conceptual diagram of the operation of the liquid medicine administration device 10) of the rotational speed of the motor 40 (a pulse signal transmitted to the motor 40 by the control unit 28) for advancing the gasket 34 and the plunger 46. The first rotational speed S1 of the motor 40 in the initial sliding period is within a range of, for example, 5.7 rpm to 34.2 rpm, preferably 5.7 rpm to 6.84 rpm. The second rotational speed S2 of the motor 40 in the normal sliding period is within a range of, for example, 34.2 rpm to 68.4 rpm, preferably 57 rpm to 68.4 rpm. The ratio of the first rotational speed S1 to the second rotational speed S2 is within a range of, for example, 8 to 80%, preferably 8 to 60%.

In the present embodiment, the control unit 28 controls the motor 40 such that the motor 40 repeatedly operates at the first rotational speed S1 and stops in the initial sliding period as shown in FIG. 4. In other words, the control unit 28 controls the motor 40 such that one cycle including one continuous rotation and one continuous stoppage of the motor 40 is repeated two or more times in the initial sliding period.

The program 28a is set such that the advancing speed of the gasket 34 according to calculation in the initial sliding period is within a range of, for example, 1 to 20 mm/min. "The advancing speed of the gasket 34 according to calculation in the initial sliding period" means the average moving speed of the gasket 34 in the initial sliding period, that is, the speed calculated by dividing the distance of the initial sliding period by the time taken for the gasket 34 to move through the initial sliding period. The program 28a is set such that an estimated advancing distance of the gasket 34 calculated based on the rotation amount of the motor 40 in one cycle in the initial sliding period is within a range of, for example, 0.01 to 0.1 mm.

The control unit 28 also controls the motor 40 such that the motor 40 repeatedly operates and stops in the normal sliding period. In other words, the control unit 28 controls the motor 40 such that one cycle including one continuous rotation and one continuous stoppage of the motor 40 is repeated two or more times in the normal sliding period.

During the intermittent driving at low speed in which the motor 40 repeatedly operates and stops in the initial sliding period, each operation time T1a is within a range of, for example, 1 to 6 seconds, preferably 1 to 2 seconds. The duty ratio, which is the ratio of the operation time T1a in one cycle including operation and stop during the intermittent driving at low speed, is within a range of, for example, 10 to 50%, preferably 10 to 25%. Due to such intermittent driving at low speed, power consumption caused by the driving of the motor 40 can be effectively reduced, as compared with the case where the motor 40 is continuously driven. The program 28a is set such that, in one cycle during intermittent driving at low speed, the rotation of the motor 40 is stopped for a predetermined time when the number of pulses transmitted to the motor 40 reaches a predetermined value corresponding to the estimated advancing distance of the gasket 34 after the motor 40 starts rotating.

During intermittent driving at high speed in which the motor repeatedly operates and stops in the normal sliding period, each operation time T2a is within a range of, for example, 83 to 500 milliseconds, preferably 166 to 333 milliseconds, and each stop time T2b is 4 to 19 times the operation time T2a, preferably 5 to 9 times the operation time T2a. The duty ratio, which is the ratio of the operation time T2a in one cycle including operation and stop during the intermittent driving is within a range of, for example, 5 to 20%, preferably 10 to 15%. Due to such intermittent driving, power consumption caused by the driving of the motor 40 can be effectively reduced, as compared with the case where the motor 40 is continuously driven.

The moving speed (the moving speed of the gasket 34 when the motor 40 rotates at the first rotational speed S1) when the gasket 34 advances in the initial sliding period is within a range of 1.0 to 20 mm per minute, preferably 1.0 to 3.0 mm per minute. The moving speed (the moving speed of the gasket 34 when the motor 40 rotates at the second rotational speed S2) when the gasket 34 advances in the normal sliding period is within a range of, for example, 7.5 to 20 mm per minute, although it depends on the administration time for administering the liquid medicine M.

In this case, the liquid medicine administration device 10 according to the first embodiment provides the following effects.

As has been described with reference to FIG. 2, when the liquid medicine administration device 10 is stored for a long time, the sliding surface (two annular protrusions 34a in the illustrated example) of the gasket 34 adheres to the inner peripheral surface of the cylinder. Therefore, when, unlike the present invention, the gasket 34 is entirely advanced at once by continuously driving the motor 40, the entire adhering portion needs to be simultaneously pulled off, which significantly increases the sliding resistance of the gasket 34.

On the other hand, according to the liquid medicine administration device 10, the gasket 34 is advanced at intervals in the initial sliding period of the gasket 34, whereby, even if the sliding surface of the gasket 34 adheres to the inner peripheral surface of the cylinder 12, the adhering portion is pulled off little by little. Thus, an excessive rise in sliding resistance in the initial sliding period can be suppressed. Accordingly, it is possible to suppress an increase in the driving force in the initial sliding period, and to provide the liquid medicine administration device 10 that is smaller in size than the conventional one.

The program 28a is set such that the stop time T1b in which the motor 40 is stopped is 1 to 55 times the operation time T1a in which the motor 40 is rotated in one cycle in the initial sliding period. Thus, because the stop time T1b of the motor 40 in one cycle in the initial sliding period is appropriately long, the adhering portion of the gasket 34 can be more reliably pulled off little by little, and an excessive rise in the sliding resistance in the initial sliding period can be further suppressed.

When the program 28a is set such that the stop time T1b in one cycle in the initial sliding period is within a range of 0.25 to 17.68 seconds, the stop time of the motor 40 in one cycle is appropriately long. Therefore, the adhering portion of the gasket 34 can be more reliably pulled off little by little, and an excessive rise in the sliding resistance in the initial sliding period can be further suppressed.

When the program 28a is set such that the advancing speed of the gasket 34 according to calculation in the initial sliding period is within a range of 1 to 20 mm/min, the driving force required to advance the gasket 34 in the initial sliding period can be sufficiently reduced.

When the program 28a is set such that the estimated advancing distance of the gasket 34 calculated based on the rotation amount of the motor 40 in one cycle is within a range of 0.01 to 0.1 mm, the driving force required to advance the gasket 34 in the first movement period can be sufficiently reduced.

The initial sliding resistance of the gasket 34 in the cylinder 12 differs depending on the moving speed of the gasket 34, and the initial sliding resistance tends to increase as the moving speed of the gasket 34 is faster, while the sliding resistance afterward does not tend to depend on the moving speed of the gasket 34. Therefore, in the initial sliding period, the sliding resistance is smaller as the moving speed of the gasket 34 is lower. On the other hand, in the normal sliding period, the sliding resistance does not tend to depend on the moving speed of the gasket 34. The length of the initial sliding period with respect to the total advancing distance of the gasket (the sum of the distance of the initial sliding period and the distance of the normal sliding period) during the operation of the liquid medicine administration device 10 is considerably small. That is, the initial sliding period is considerably shorter than the normal sliding period.

In view of this, the liquid medicine administration device 10 executes low-speed driving in which the gasket 34 is slowly moved by rotating the motor 40 at the first rotational speed S1 in the initial sliding period, and executes high-speed driving in which the gasket 34 is quickly moved by rotating the motor 40 at the second rotational speed S2 in the normal sliding period following the initial sliding period.

Therefore, the driving force required to advance the plunger 46 (required thrust) in the initial sliding period is suppressed, whereby a desired administration rate is achieved without an increase in power consumption. That is, when, unlike the present embodiment, the plunger 46 is driven at high speed in the initial sliding period as indicated by a broken line L2 in FIG. 5, the sliding resistance of the gasket 34 with respect to the cylinder 12 considerably increases. In this case, if large power is supplied to the motor 40 in response to a large sliding resistance without changing the motor 40, the power consumption increases. A high-cost motor or a large-sized motor is required to obtain required driving force without increasing power consumption.

Figure 5:
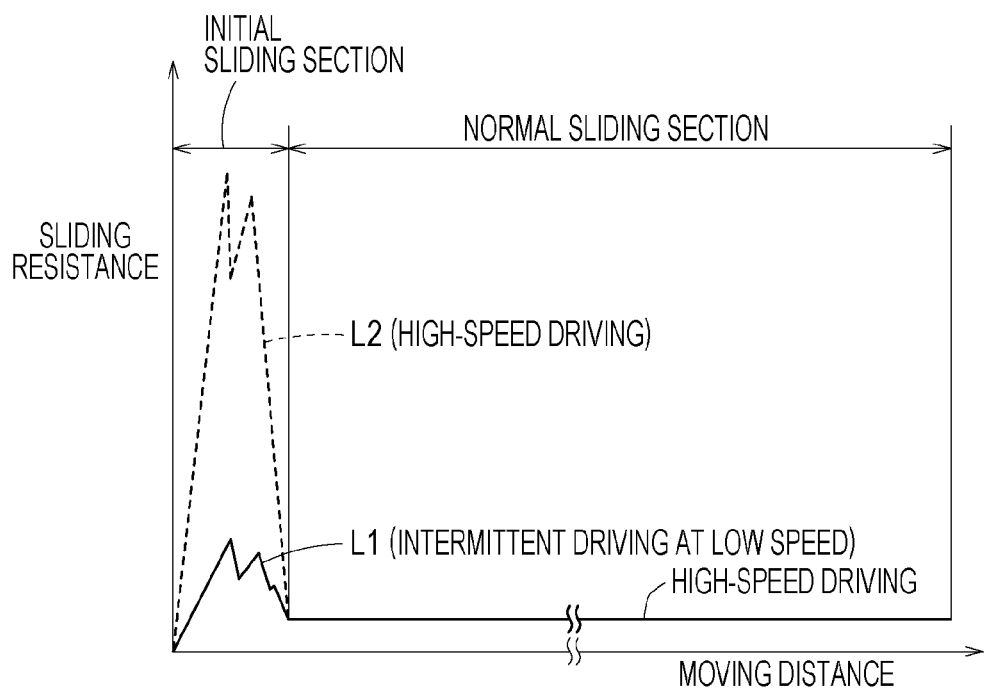
FIG. 5 is a second diagram for describing the action of the liquid medicine administration device according to the first embodiment.

On the other hand, when the plunger 46 is driven at low speed in the initial sliding period, the sliding resistance of the gasket 34 with respect to the cylinder 12 is considerably smaller than that of the gasket 34 driven at high speed in the initial sliding period, as indicated by a solid line L1 in FIG. 5. Therefore, the liquid medicine administration device 10 can suppress an increase in power consumption and can administer the liquid medicine M at a desired administration rate without using a high-cost motor or a large-sized motor.

In the liquid medicine administration device 10, it is preferable that the maximum value of the sliding resistance of the gasket 34 in the initial sliding period is 8 N or less by the motor 40 operating at the first rotational speed S1. Thus, the power consumption by the driving of the motor 40 can be reduced effectively.

Figure 6:
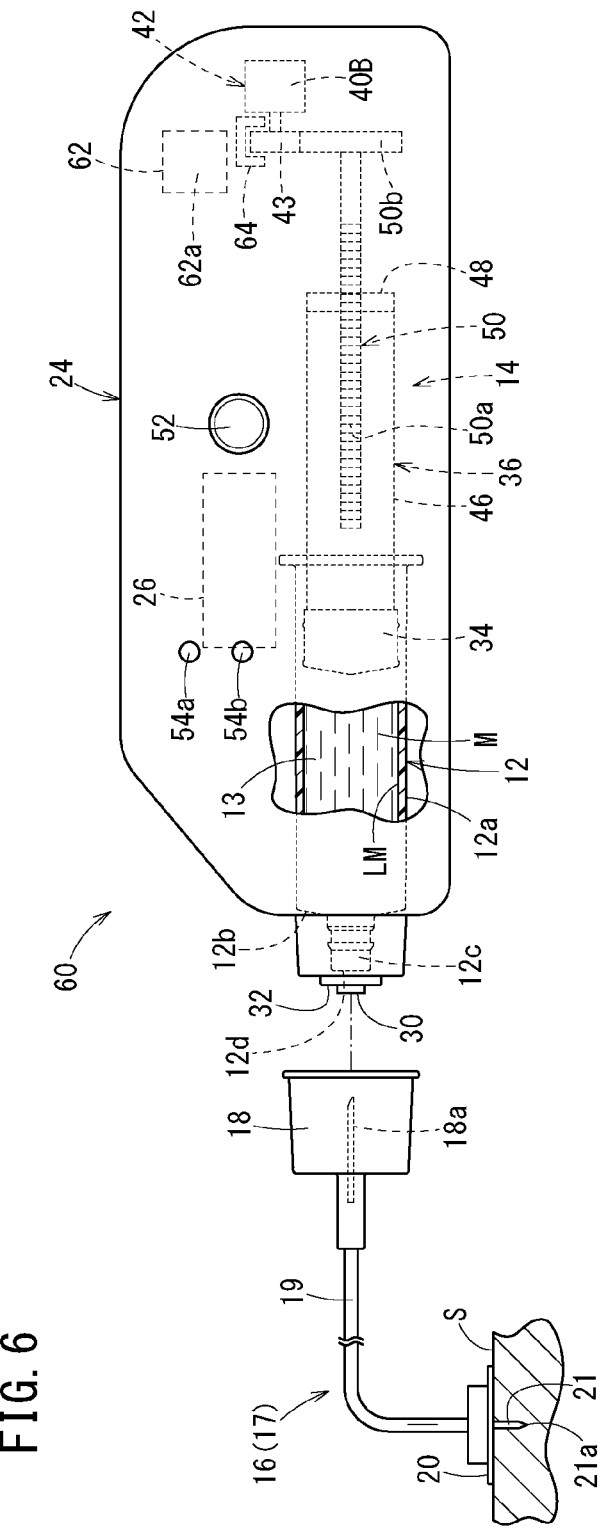
FIG. 6 is a schematic view of a liquid medicine administration device according to a second embodiment of the present invention.

Next, a liquid medicine administration device 60 according to a second embodiment shown in FIG. 6 will be described.

In the liquid medicine administration device 60, a DC motor is used as a motor 40B that drives the advancing mechanism 36. In the liquid medicine administration device 60, a control unit 62 controls the operation of the motor 40B. The control unit 62 has a program 62a set such that one cycle including one continuous rotation and one continuous stoppage of the motor 40B is repeated two or more times in the initial sliding period.

The program 62a is set such that a time CT1 of one cycle in the initial sliding period is within a range of, for example, 0.5 to 18 seconds. The program 62a is set such that an operation time T1a in which the motor 40B is rotated in one cycle in the initial sliding period is within a range of, for example, 0.067 to 2 seconds. The motor 40B is a DC motor. Therefore, if the same voltage is applied to the motor 40B, the operation time T1a becomes longer as a load (torque load) applied to the motor 40B due to the sliding resistance of the gasket 34 is greater, and the operation time T1a becomes shorter as the load is smaller.

The program 62a is set such that, in one cycle in the initial sliding period, a stop time T1b in which the motor 40B is stopped is, for example, 1 to 55 times the operation time T1a in which the motor 40B is rotated. The program 62a is set such that the stop time T1b in one cycle in the initial sliding period is within a range of, for example, 0.25 to 17.68 seconds. The program 62a is set such that the advancing speed of the gasket 34 according to calculation in the initial sliding period is within a range of, for example, 1 to 20 mm/min. The program 62a is set such that the estimated advancing distance of the gasket 34 calculated based on the rotation amount of the motor 40B in one cycle in the initial sliding period is within a range of, for example, 0.01 to 0.1 mm. Note that the configuration in which the stop time T1b in one cycle in the initial sliding period is set to be 1 to 55 times the operation time T1a includes a configuration in which the stop time T1b is set to be 1 to 55 times the operation time T1a by the program 62a controlling the time of one cycle and the rotation amount of the motor 40B in the initial sliding period.

The liquid medicine administration device 60 includes a rotation amount detection sensor 64 (rotary encoder) that detects the rotation amount of the motor 40B. According to one aspect, the rotation amount detection sensor 64 is an optical transmissive encoder having a light emitting element and a light receiving element, and a pinion 43 functioning as a code wheel has a plurality of slits formed at intervals in the circumferential direction. A light transmission pattern is detected by the rotation amount detection sensor 64. The rotational direction and the rotation amount of the motor 40B can be detected from the light transmission pattern. The program 62a is set such that, in one cycle in the initial sliding period, the rotation of the motor 40B is stopped for a predetermined time when the rotation amount of the motor 40B detected by the rotation amount detection sensor 64 after the motor 40B starts rotating reaches a predetermined value corresponding to the estimated advancing distance of the gasket 34.

Next, the operation of the liquid medicine administration device 60 will be described. In the following, a first operation method (FIGS. 7 and 8) in which the control on the motor operation is not switched over the entire range of the initial sliding period and the normal sliding period and a second operation method (FIGS. 9 to 12) for switching the control on the motor operation with the transition from the initial sliding period to the normal sliding period will be described.

Figure 7:
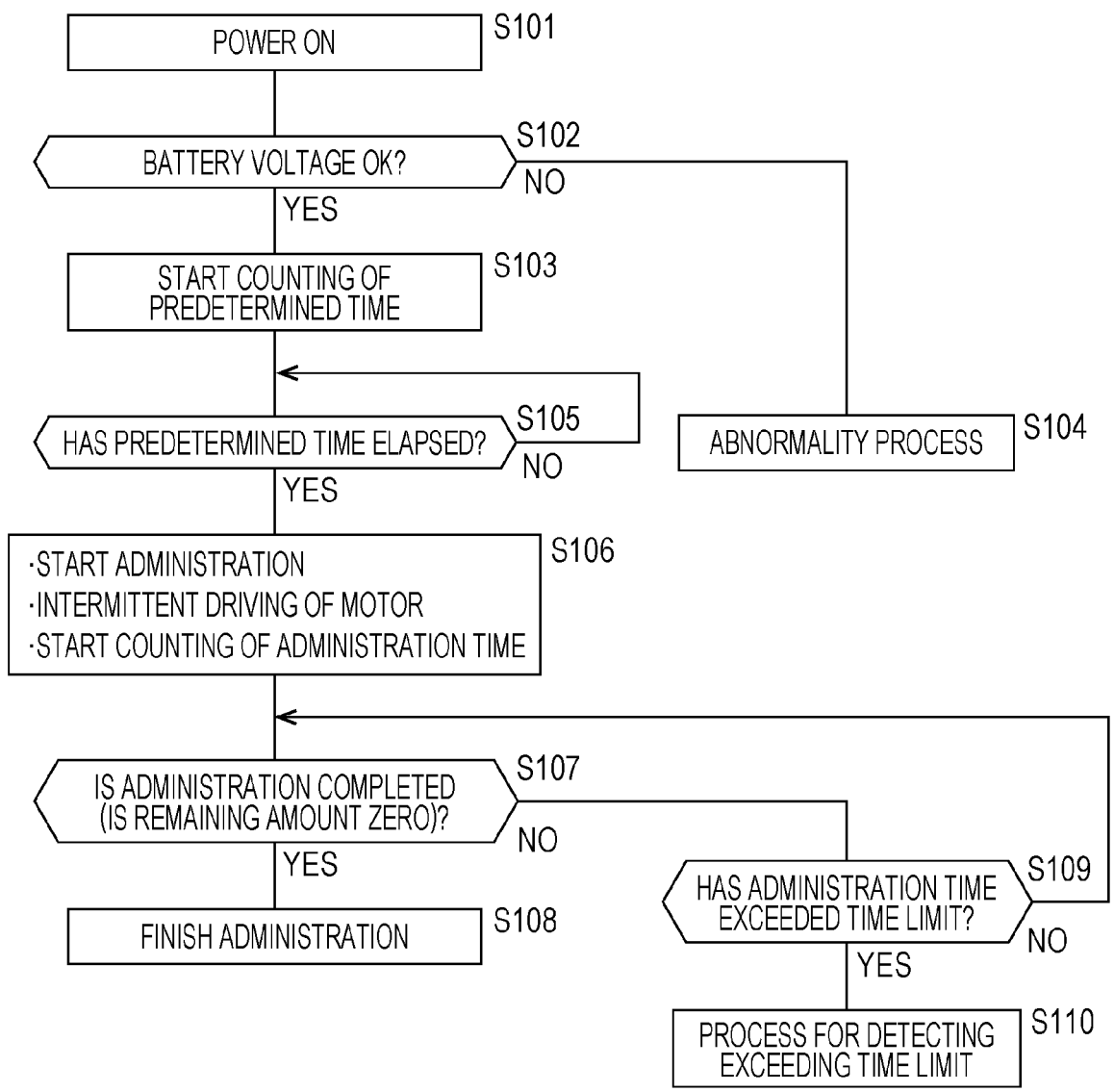
FIG. 7 is a flowchart for describing an operation (first operation method) of the liquid medicine administration device according to the second embodiment.

In the first operation method, when a power button 52 (FIG. 6) of the liquid medicine administration device 60 is pressed and the power is turned on (step S101), a process for checking a battery voltage is executed (step S102), as shown in FIG. 7. If it is determined that there is no abnormality in the battery voltage ("YES" in step S102), a user is notified that there is no abnormality, and counting of a predetermined time (for example, 5 minutes) is started (step S103). Next, the liquid medicine administration device 60 is attached to the patient. When there is an abnormality in the battery voltage ("NO" in step S102), an abnormality process is performed (step S104).

When a predetermined time has elapsed after step S103 ("YES" in step S105), the control unit 62 of the liquid medicine administration device 60 drives the motor 40B to start administration (start intermittent driving of the motor 40B), and starts counting of an administration time (step S106). In this case, the voltage applied to the motor 40B is the same in the initial sliding period and the normal sliding period. That is, the control unit 62 does not change the control on the motor 40B in the initial sliding period and the normal sliding period.

When the administration with intermittent driving is performed, and the control unit 62 determines that the administration is completed (the remaining amount of the liquid medicine is zero) ("YES" in step S107), the administration is finished (step S108). If it is not determined that the administration has been completed ("NO" in step S107) and it is determined that the administration time exceeds a time limit ("YES" in step S109), the control unit 62 performs a process for detecting exceeding time limit (step S110).

Figure 8:
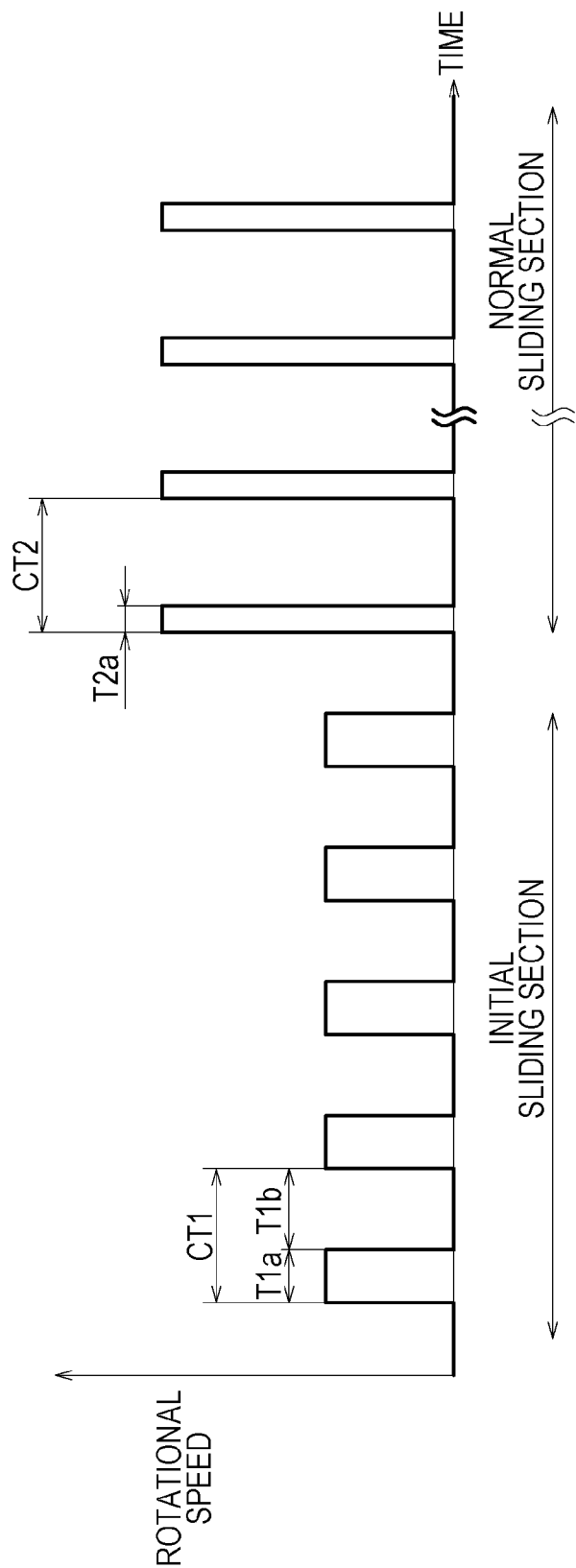
FIG. 8 is a conceptual diagram illustrating an operation of the liquid medicine administration device according to the second embodiment in accordance with the first operation method.
Figure 9:
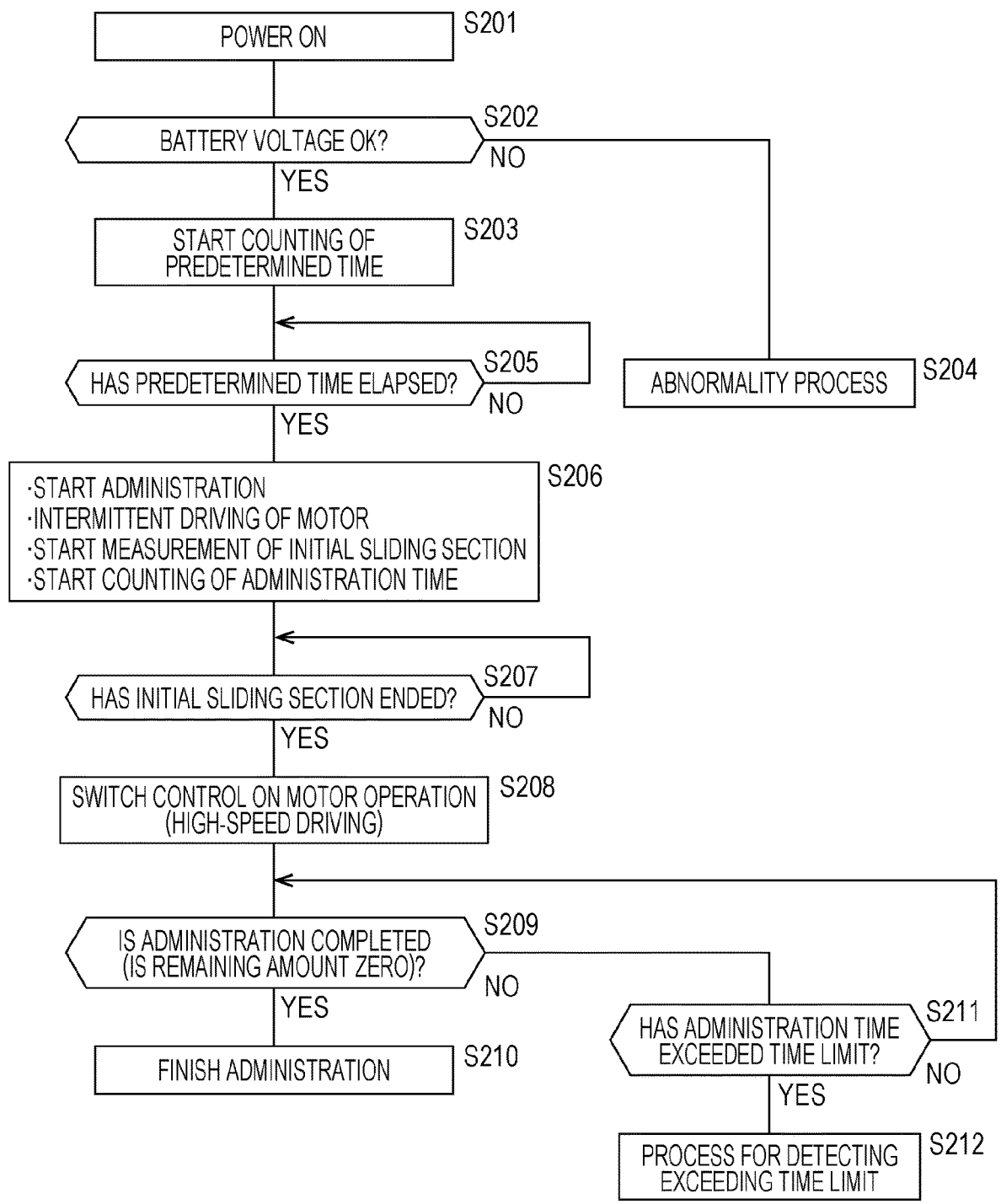
FIG. 9 is a flowchart for describing an operation (second operation method) of the liquid medicine administration device according to the second embodiment.

FIG. 8 is a conceptual diagram of the operation of the liquid medicine administration device 60 when the first operation method is performed. In FIG. 8, the time CT1 of one cycle in the initial sliding period and a time CT2 of one cycle in the normal sliding period are set to be the same. An operation time T2a of the motor 40B in one cycle in the normal sliding period is set shorter than the operation time T1a of the motor 40B in one cycle in the initial sliding period.

Because the motor 40B is a DC motor, the rotational speed of the motor 40B changes depending on the load (torque load) applied to the motor 40B due to the sliding resistance of the gasket 34. Therefore, the control unit 62 does not directly control the rotational speed of the motor 40B. On the other hand, when the gasket 34 transfers from the initial sliding period to the normal sliding period, the sliding resistance of the gasket 34 decreases, which leads to a decrease in load on the motor 40B. As a result, the rotational speed of the motor 40B naturally increases with the transition from the initial sliding period to the normal sliding period, although the voltage applied to the motor 40B is unchanged. In other words, the rotational speed of the motor 40B in the normal sliding period is higher than the rotational speed of the motor 40B in the initial sliding period.

Note that FIG. 8 shows as if the motor 40B rotates at the same rotational speed in all cycles in the initial sliding period, and the motor 40B also rotates at the same rotational speed in all cycles in the normal sliding period. However, because the rotational speed of the motor 40B varies depending on the load applied to the motor 40B as described above, the motor 40B does not necessarily rotate at the same rotational speed in the cycles in the initial sliding period in actuality. Similarly, the motor 40B does not necessarily rotate at the same rotational speed in the cycles in the normal sliding period in actuality.

Next, the second operation method of the liquid medicine administration device 60 will be described. In the second operation method, the control unit 62 switches control on the motor operation along with the transition from the initial sliding period to the normal sliding period. The flowchart showing the second operation method in FIG. 9 differs from the first operation method in that steps S206 to S208 are performed instead of step S106 in the flowchart showing the first operation method in FIG. 7.

Steps S201 to S205 are the same as steps S101 to S105 of the first operation method, respectively. In the second operation method, when a predetermined time has elapsed after step S203 ("YES" in step S205), the control unit 62 drives the motor 40B to start administration (start intermittent driving of motor 40B), starts measurement of the initial sliding period, and starts counting of administration time (step S206).

Next, the control unit 62 determines whether or not the initial sliding period has ended (step S207). The distance the gasket 34 advances can be calculated by multiplying the rotation amount of the motor 40B detected by the rotation amount detection sensor 64 by the distance the gasket 34 advances in one rotation of the motor 40B. Therefore, the control unit 62 can determine whether or not the initial sliding period has ended on the basis of the rotation amount of the motor 40B obtained by the rotation amount detection sensor 64.

When the initial sliding period has ended ("YES" in step S207), the control unit 62 of the liquid medicine administration device 60 switches control on the motor operation (transfers to high-speed driving) (step S208). The subsequent steps S209 to S212 are the same as steps S107 to S110 of the first operation method, respectively.

Some modes may be adopted as the process to be executed in step S208 (switching of control on motor operation), and the present specification shows a first mode (FIG. 10), a second mode (FIG. 11), and a third mode (FIG. 12) below as examples.

Figure 10:
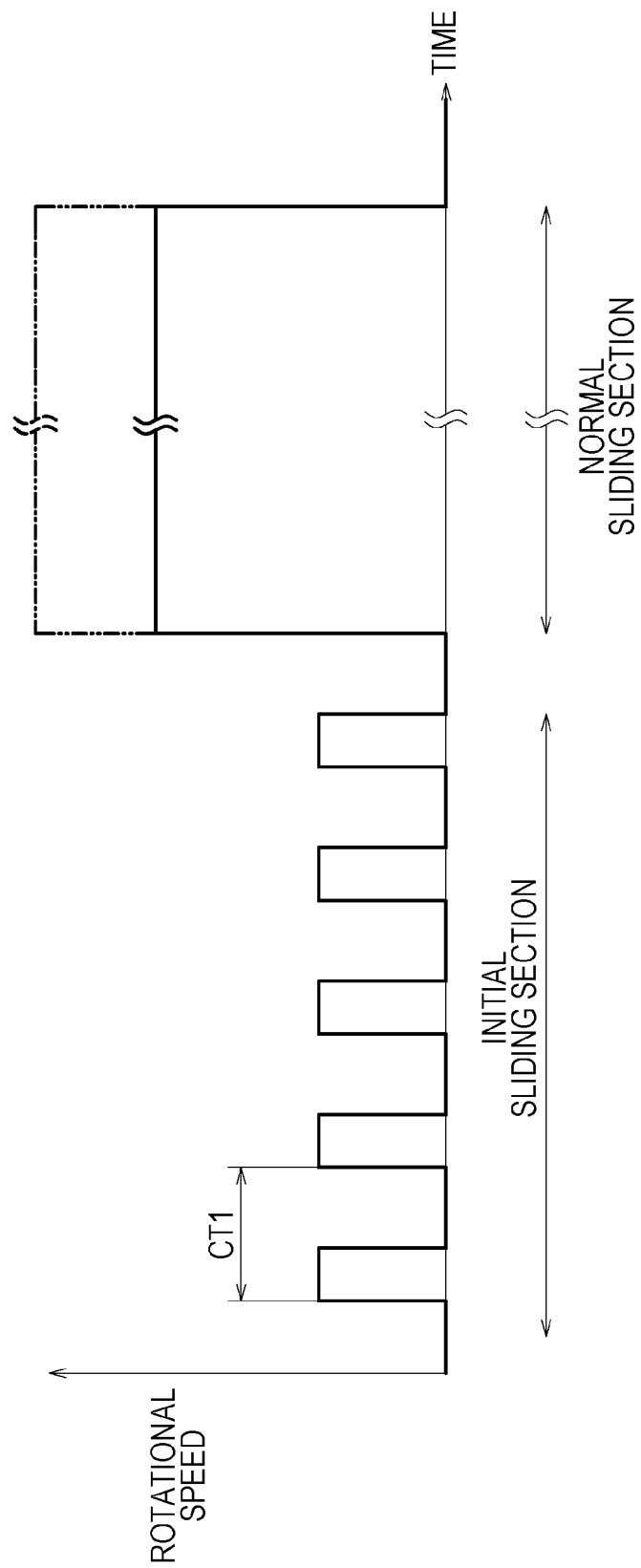
FIG. 10 is a conceptual diagram illustrating an operation of the liquid medicine administration device according to the second embodiment in accordance with the second operation method (first mode).

As shown in FIG. 10, in the first mode of switching of control on the motor operation, the motor 40B is continuously driven in the entire area of the normal sliding period. That is, the stop time of the motor 40B is not provided in the normal sliding period. In this case, the voltage applied to the motor 40B is the same between the initial sliding period and the normal sliding period. However, due to a decrease in sliding resistance in the normal sliding period, the rotational speed of the motor 40B increases. As described above, the motor 40B is continuously driven in the entire area of the normal sliding period, whereby the administration time can be shortened as compared with the first operation method.

Note that, in the first mode, the voltage applied to the motor 40B in the normal sliding period may be set higher than the voltage applied to the motor 40B in the initial sliding period. As the applied voltage is higher, the rotational speed of the motor 40B increases more. Therefore, when the voltage applied to the motor 40B is increased, the rotational speed of the motor 40B in the normal sliding period further increases as shown by a phantom line. This can further reduce the administration time.

Figure 11:
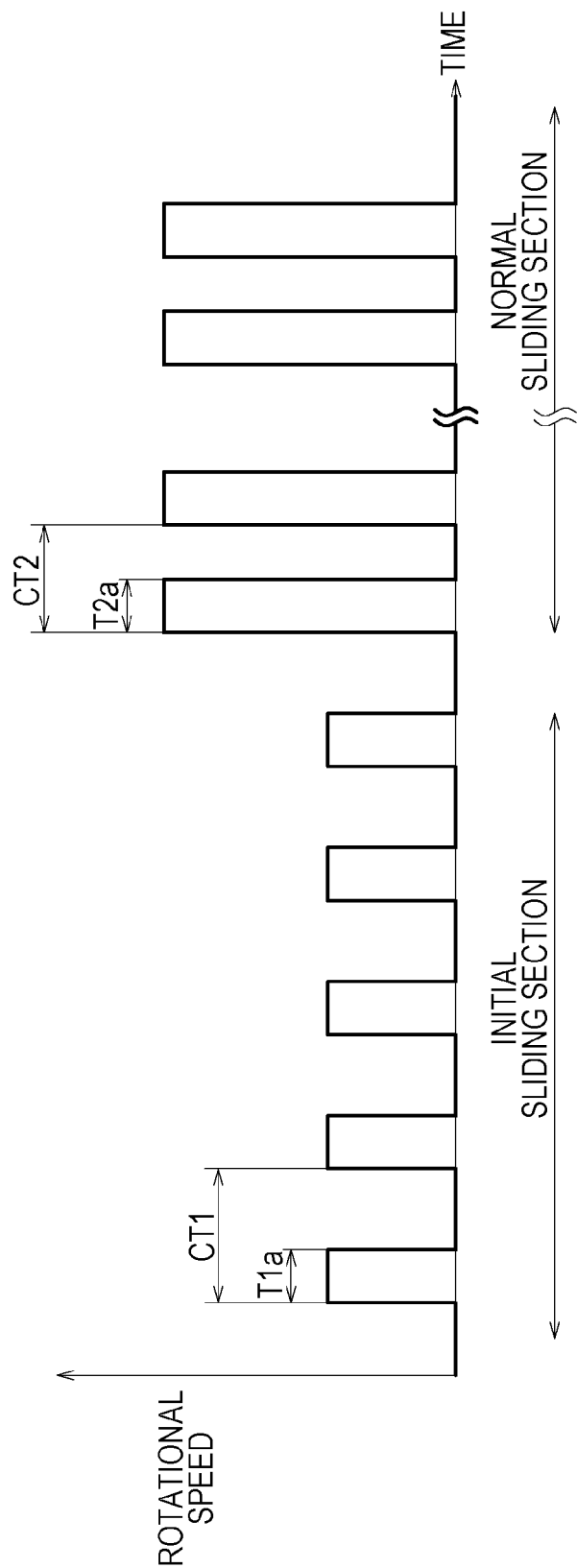
FIG. 11 is a conceptual diagram illustrating an operation of the liquid medicine administration device according to the second embodiment in accordance with the second operation method (second mode).

As shown in FIG. 11, in the second mode of switching of control on motor operation, the operation time T2a of the motor 40B in one cycle in the normal sliding period is equal to the operation time T1a of the motor 40B in one cycle in the initial sliding period, and the motor 40B is intermittently driven in the normal sliding period. However, the time CT2 of one cycle in the normal sliding period is set shorter than the time CT1 of one cycle in the initial sliding period. Thus, the administration time can be shortened as compared with the first operation method. The time CT2 of one cycle in the normal sliding period is, for example, 0.02 to 0.5 times the time CT1 of one cycle in the initial sliding period. Note that the voltage applied to the motor 40B in the normal sliding period may be set higher than the voltage applied to the motor 40B in the initial sliding period.

Figure 12:
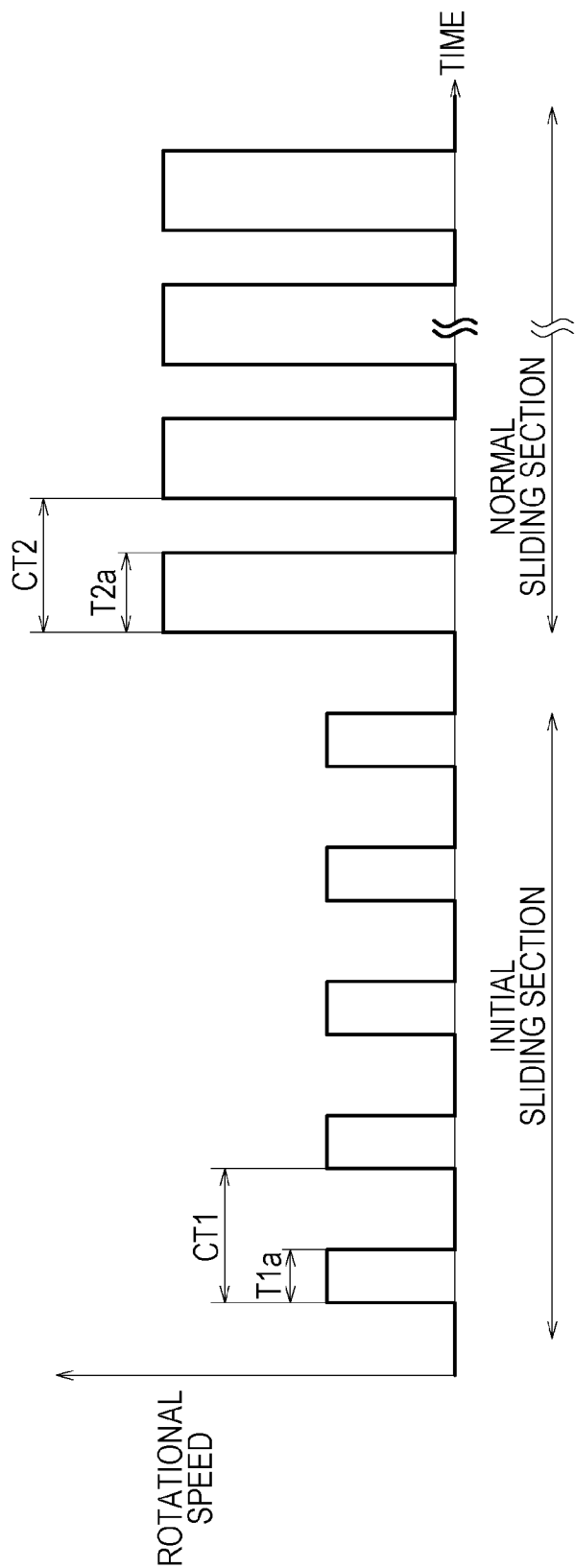
FIG. 12 is a conceptual diagram illustrating an operation of the liquid medicine administration device according to the second embodiment in accordance with the second operation method (third mode).

As shown in FIG. 12, in the third mode of switching of control on motor operation, the time CT1 of one cycle in the initial sliding period is equal to the time CT2 of one cycle in the normal sliding period, and the motor 40B is intermittently driven in the normal sliding period. However, the operation time T2a of the motor 40B in one cycle in the normal sliding period is set longer than the operation time T1a of the motor 40B in one cycle in the initial sliding period. Thus, the administration time can be shortened as compared with the first operation method. The operation time T2a of the motor 40B in one cycle in the normal sliding period is, for example, 1.5 to 18 times the operation time T1a of the motor 40B in one cycle in the initial sliding period. Note that the time CT2 of one cycle in the normal sliding period may be set shorter than the time CT1 of one cycle in the initial sliding period. The voltage applied to the motor 40B in the normal sliding period may be set higher than the voltage applied to the motor 40B in the initial sliding period.

According to the liquid medicine administration device 60 configured as described above, the gasket 34 is advanced at intervals in the initial sliding period of the gasket 34, whereby, even if the sliding surface of the gasket 34 adheres to the inner peripheral surface of the cylinder 12, the adhering portion is pulled off little by little, as with the above-mentioned liquid medicine administration device 10. Thus, an excessive rise in sliding resistance in the initial sliding period can be suppressed. Accordingly, it is possible to suppress an increase in the driving force in the initial sliding period, and to provide the liquid medicine administration device 60 that is smaller in size than the conventional one.

The present invention is not limited to the embodiments described above, and various modifications can be made without departing from the scope of the present invention.

The invention claimed is:

1. A liquid medicine administration device for administering a liquid medicine into a living body, comprising:
a cylinder filled with the liquid medicine;
a gasket located inside the cylinder in a slidable manner;
a liquid lubricant disposed on an inner peripheral surface of the cylinder or an outer peripheral surface of the gasket;
an advancing mechanism configured to advance the gasket in a distal direction;
a drive mechanism comprising a motor that is configured to drive the advancing mechanism;
a battery configured to supply power to the motor; and
a control unit programmed to control an operation of the motor to drive the advancing mechanism and thereby advance the gasket during (i) a first movement period from a time when only a part of the gasket starts moving until a time when an entirety of the gasket starts moving, and (ii) a second movement period following the first movement period;
wherein the control unit is programmed to control the motor to repeat, two or more times during the first movement period, a cycle that includes one period of continuous rotation of the motor and one period of continuous stoppage of the motor.

2. The liquid medicine administration device according to claim 1,
wherein the control unit is programmed such that, during the cycle, a stop time during which the motor is stopped is 1 to 55 times an operation time during which the motor is rotated.

3. The liquid medicine administration device according to claim 1,
wherein the control unit is programmed such that, during the cycle, a stop time during which the motor is stopped is within a range of 0.25 to 17.68 seconds.

4. The liquid medicine administration device according to claim 1,
wherein the control unit is programmed such that, during the first movement period, an advancing speed of the gasket is within a range of 1 to 20 mm/min.

5. The liquid medicine administration device according to claim 1,
wherein the control unit comprises a rotation amount detection sensor configured to detect a rotation amount of the motor; and
the control unit is programmed such that, during the cycle, the rotation of the motor is stopped for a predetermined time when a rotation amount of the motor detected by the rotation amount detection sensor after the motor starts rotating reaches a predetermined value.

6. The liquid medicine administration device according to claim 1,
wherein the motor is a stepping motor;
the control unit is programmed to control a frequency of a pulse transmitted to the motor; and
the control unit is programmed such that, during the cycle, the rotation of the motor is stopped for a predetermined time when the number of pulses transmitted to the motor reaches a predetermined value.

7. The liquid medicine administration device (10, 60) according to claim 1,
wherein the control unit is programmed such that, during the cycle, an estimated advancing distance of the gasket calculated based on a rotation amount of the motor is within a range of 0.01 to 0.1 mm.

8. The liquid medicine administration device according to claim 7,
wherein the control unit comprises a rotation amount detection sensor configured to detect a rotation amount of the motor; and
the control unit is programmed such that, during the cycle, the rotation of the motor is stopped for a predetermined time when a rotation amount of the motor detected by the rotation amount detection sensor after the motor starts rotating reaches a predetermined value corresponding to the estimated advancing distance of the gasket.

9. The liquid medicine administration device according to claim 7,
wherein the motor is a stepping motor;
the control unit is programmed to control a frequency of a pulse transmitted to the motor; and
the control unit is programmed such that, during the cycle, the rotation of the motor is stopped for a predetermined time when the number of pulses transmitted to the motor reaches a predetermined value corresponding to the estimated advancing distance of the gasket after the motor starts rotating.

10. The liquid medicine administration device according to claim 1,
wherein the control unit is programmed to control the operation of the motor such that an advancing speed of the gasket during the second movement period is faster than an advancing speed of the gasket during the first movement period.

11. An method for operating a liquid medicine administration device, comprising:
providing the liquid medicine administration device, which comprises:
a cylinder filled with the liquid medicine,
a gasket located inside the cylinder in a slidable manner,
a liquid lubricant disposed on an inner peripheral surface of the cylinder or an outer peripheral surface of the gasket,
an advancing mechanism configured to advance the gasket in a distal direction,
a drive mechanism comprising a motor that is configured to drive the advancing mechanism,
a battery configured to supply power to the motor, and
a control unit programmed to control an operation of the motor to drive the advancing mechanism and thereby advance the gasket during (i) a first movement period from a time when only a part of the gasket starts moving until a time when an entirety of the gasket starts moving, and (ii) a second movement period following the first movement period; and
controlling, with the control unit, operation of the motor to repeat, two or more times during the first movement period, a cycle that includes one period of continuous rotation of the motor and one period of continuous stoppage of the motor.

12. The method according to claim 11,
wherein, during the cycle, a stop time during which the motor is stopped is 1 to 55 times an operation time during which the motor is rotated.

13. The method according to claim 11,
wherein a stop time of the motor during the cycle is within a range of 0.25 to 17.68 seconds.

14. The method according to claim 11,
wherein the control unit comprises a rotation amount detection sensor that detects a rotation amount of the motor; and
during the cycle, the rotation of the motor is stopped when an estimated advancing distance of the gasket calculated based on a rotation amount of the motor detected by the rotation amount detection sensor reaches a value within a range of 0.01 to 0.1 mm.

15. A non-transient computer-readable medium programmed to control a liquid medicine administration device for administering a liquid medicine into a living body that comprises a cylinder filled with the liquid medicine, a gasket located inside the cylinder in a slidable manner, a liquid lubricant disposed on an inner peripheral surface of the cylinder or an outer peripheral surface of the gasket, an advancing mechanism configured to advance the gasket in a distal direction, a drive mechanism comprising a motor that is configured to drive the advancing mechanism, and a battery configured to supply power to the motor, wherein the non-transient computer-readable medium comprises a program for performing steps comprising:
controlling an operation of the motor to drive the advancing mechanism and thereby advance the gasket during (i) a first movement period from a time when only a part of the gasket starts moving until a time when an entirety of the gasket starts moving, and (ii) a second movement period following the first movement period; and
controlling the motor to repeat, two or more times during the first movement period, a cycle that includes one period of continuous rotation of the motor and one period of continuous stoppage of the motor.

* * * * *